United States Patent
Setsuda et al.

(10) Patent No.: US 10,345,231 B2
(45) Date of Patent: Jul. 9, 2019

(54) SIGNAL DETECTION DEVICE AND OPTICAL CHARACTERISTICS MEASUREMENT DEVICE

(71) Applicant: Yokogawa Electric Corporation, Tokyo (JP)

(72) Inventors: Kazuki Setsuda, Tokyo (JP); Naomichi Chida, Tokyo (JP); Kazufumi Nishida, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 38 days.

(21) Appl. No.: 15/822,398

(22) Filed: Nov. 27, 2017

(65) Prior Publication Data

US 2018/0149587 A1 May 31, 2018

(30) Foreign Application Priority Data

Nov. 29, 2016 (JP) .................................. 2016-231348

(51) Int. Cl.
*G01N 21/3559* (2014.01)
*H03F 3/08* (2006.01)
(Continued)

(52) U.S. Cl.
CPC ..... *G01N 21/3559* (2013.01); *G01N 21/3151* (2013.01); *H03F 3/085* (2013.01); *H03F 3/087* (2013.01); *G01N 21/359* (2013.01)

(58) Field of Classification Search
CPC ..... H03F 3/085; H03F 3/087; G01N 21/3151; G01N 21/3559; G01N 21/359; G01N 21/35

See application file for complete search history.

(56) References Cited

U.S. PATENT DOCUMENTS

| 2009/0027655 A1* | 1/2009 | Haran ............... G01N 21/55 356/51 |
| 2010/0245834 A1* | 9/2010 | Strandjord ........... G01C 19/721 356/463 |
| 2012/0019815 A1 | 1/2012 | Horikoshi et al. |

FOREIGN PATENT DOCUMENTS

JP 5429494 B2 2/2014

OTHER PUBLICATIONS

"Model 7270 DSP Lock-in Amplifier Instruction Manual," Ametek Advanced Measurement Technology, Inc., 2010 (11 pages total).
(Continued)

*Primary Examiner* — David P Porta
*Assistant Examiner* — Fani Boosalis
(74) *Attorney, Agent, or Firm* — Sughrue Mion, PLLC

(57) ABSTRACT

A signal detection device according to one aspect of the present invention includes a receiver configured to receive a signal including at least a first signal component modulated by a first frequency and a second signal component modulated by a second frequency, and a detector configured to generate, using a base signal, a first reference signal to be used for detecting the first signal component and a second reference signal to be used for detecting the second signal component, perform lock-in detection on the signal received by the receiver using the first reference signal to obtain a first detection signal, perform lock-in detection on the signal received by the receiver using the second reference signal to obtain two second detection signals having different phases from each other, and change at least one of a frequency and a phase of each of the first and second reference signals to set one of the two second detection signals to zero.

20 Claims, 8 Drawing Sheets

(51) Int. Cl.
*G01N 21/31* (2006.01)
*G01N 21/359* (2014.01)

(56) References Cited

OTHER PUBLICATIONS

"Model 7270 DSP Lock-in Amplifier Instruction Manual," Ametek Advanced Measurement Technology, Inc., 2010, 4 pgs.

* cited by examiner

| ADDRESS i | M(i) | N(i) |
|---|---|---|
| 0 | cos(10*π*0/256) | sin(10*π*0/256) |
| 1 | cos(10*π*1/256) | sin(10*π*1/256) |
| ⋮ | ⋮ | ⋮ |
| i | cos(10*π*i/256) | sin(10*π*i/256) |
| ⋮ | ⋮ | ⋮ |
| 255 | cos(10*π*255/256) | sin(10*π*255/256) |

FIG. 7

| ADDRESS i | L(i) | M(i) | N(i) | P(i) |
|---|---|---|---|---|
| 0 | cos(8*π*0/256) | cos(10*π*0/256) | sin(10*π*0/256) | cos(12*π*0/256) |
| 1 | cos(8*π*1/256) | cos(10*π*1/256) | sin(10*π*1/256) | cos(12*π*1/256) |
| ... | ... | ... | ... | ... |
| i | cos(8*π*i/256) | cos(10*π*i/256) | sin(10*π*i/256) | cos(12*π*i/256) |
| ... | ... | ... | ... | ... |
| 255 | cos(8*π*255/256) | cos(10*π*255/256) | sin(10*π*255/256) | cos(12*π*255/256) |

SIGNAL DETECTION DEVICE AND OPTICAL CHARACTERISTICS MEASUREMENT DEVICE

BACKGROUND OF THE INVENTION

Field of the Invention

The present invention relates to a signal detection device and an optical characteristics measurement device.

The present application claims priority based on Japanese patent application 2016-231348, filed on Nov. 29, 2016 and includes herein by reference the content thereof.

Description of Related Art

An optical characteristics measurement device radiates light to a measurement target and receives light having passed through the measurement target or light reflected or scattered from the measurement target to thereby measure optical characteristics (for example, transmission or reflection characteristics) of the measurement target. This optical characteristics measurement device can measure the optical characteristics of a measurement target without destroying the measurement target and is therefore used in a variety of fields. For example, in the paper manufacturing field, the optical characteristics measurement device may be used as a moisture meter for measuring a moisture content contained in paper which is a product online and a basis weight sensor for measuring a weight of paper online.

The moisture meter irradiates a plurality of near-infrared radiations of different wavelengths to paper which is a measurement target, receives near-infrared radiation having passed through the paper, calculates the absorption ratios thereof, and measures a moisture content contained in the paper by referring to a relationship between a paper moisture content and an absorption ratio of near-infrared radiation measured in advance. For example, near-infrared radiation with a wavelength of 1.94 μm, having a high absorption ratio in water, near-infrared radiation with a wavelength of 2.1 μm, having a high absorption ratio in cellulose which is a main component of paper, and near-infrared radiation with a wavelength of 1.7 μm, having a low absorption ratio in water and cellulose may be used as the near-infrared radiation to be irradiated to paper.

Japanese Patent Publication No. 5429494 (hereinafter, referred to as "Patent Document 1") discloses an optical characteristics measurement device in the related art which suppresses the influence of noise by distinguishing between a plurality of optical signals obtained by one optical receiver receiving the plurality of near-infrared radiations described above without them being mixed with each other. Specifically, in Patent Document 1, a plurality of near-infrared radiations having different wavelengths are modulated using different frequencies, and lock-in detection of optical signals received by one optical receiver is performed using different frequencies (the same frequencies as the frequencies used for modulation of the near-infrared radiation) so that a plurality of optical signals are distinguished without them being mixed with each other.

"Model 7270 DSP Lock-in Amplifier Instruction Manual". AMETEK ADVANCED MEASUREMENT TECHNOLOGY, INC (hereinafter, referred to as "Non-Patent Document 1") discloses a lock-in amplifier which is configured to be able to output two signals (X and Y) of different phases and capable of performing lock-in detection without using a reference signal by controlling the signals so that the output of one signal (for example, Y) reaches zero. In Non-Patent Document 1, an operation mode of performing lock-in detection without using a reference signal is referred to as a virtual reference mode.

Lock-in detection is generally a detection method of multiplying a measurement signal by a reference signal to obtain a signal and removing a high-frequency component of the obtained signal to thereby detect a specific signal. Due to this, a reference signal is basically necessary to perform lock-in detection.

In Patent Document 1 described above, an illumination device that emits near-infrared radiation is electrically connected to a light receiving device that receives the near-infrared ray, and a signal generated by a signal generator (a device for generating a modulation signal for modulating a near-infrared ray) provided in the illumination device is input to a lock-in amplifier provided in the light receiving device as a reference signal. However, since such a configuration requires electrical connection means (for example, wirings or a communication device) for transferring a reference signal from the illumination device to the light receiving device, there are some cases in which the configuration or installation of the device is limited.

In Non-Patent Document 1 described above, since lock-in detection can be performed without using a reference signal, it is considered that such a problem as in Patent Document 1 described above does not occur. However, in Non-Patent Document 1 described above, one lock-in amplifier capable of outputting two signals of different phases is required for one signal. Due to this, when the lock-in amplifier disclosed in Non-Patent Document 1 described above is used for detecting a plurality of optical signals as in Patent Document 1 described above, a plurality of lock-in amplifiers are required. As a result, there are some cases in which the size, the weight, and the cost of the device are increased.

SUMMARY OF THE INVENTION

One aspect of the present invention provides a signal detection device and an optical characteristics measurement device which are small-sized, lightweight, and inexpensive and are capable of detecting a plurality of signals without using a reference signal.

A signal detection device according to a first aspect of the present invention may include a receiver configured to receive a signal including at least a first signal component modulated by a first frequency and a second signal component modulated by a second frequency, and a detector configured to generate, using a base signal, a first reference signal to be used for detecting the first signal component and a second reference signal to be used for detecting the second signal component, perform lock-in detection on the signal received by the receiver using the first reference signal to obtain a first detection signal, perform lock-in detection on the signal received by the receiver using the second reference signal to obtain two second detection signals having different phases from each other, and change at least one of a frequency and a phase of each of the first and second reference signals to set one of the two second detection signals to zero.

In the above-described signal detection device, the detector may include a reference oscillator configured to oscillate the base signal of which the frequency is variable, a divider configured to perform frequency dividing of the base signal to generate the first and second reference signals, a first lock-in amplifier configured to multiply the first reference signal output from the divider by the signal received by the receiver to generate the first detection signal, and a second lock-in amplifier configured to multiply the second reference signal output from the divider by the signal received by the receiver to generate the two second detection signals. The reference oscillator may be controlled to change the frequency of the base signal to change the at least one of the frequency and the phase of each of the first and second reference signals.

In the above-described signal detection device, the second lock-in amplifier may be configured to multiply the second reference signal output from the divider by the signal received by the receiver and multiply a third reference signal, which is obtained by shifting the phase of the second reference signal, by the signal received by the receiver to generate the two second detection signals having different phases from each other.

In the above-described signal detection device, the second lock-in amplifier may be configured to input the second detection signal generated by multiplying the third reference signal by the signal received by the receiver into the reference oscillator.

In the above-described signal detection device, the reference oscillator may be configured to change the frequency of the base signal to set the second detection signal input from the second lock-in amplifier to zero.

In the above-described signal detection device, the first and second reference signals may have different frequencies from each other.

In the above-described signal detection device, the detector may include a reference oscillator configured to oscillate the base signal of which the frequency is variable, and a dual-phase lock-in amplifier configured to operate in synchronization with the base signal to generate the second detection signals. The dual-phase lock-in amplifier may include a digital converter configured to convert the signal received by the receiver to a digital signal, a memory storing a sine wave data array and a cosine wave data array to be used as the second reference signal, a first multiplier configured to sequentially read one of the sine wave data array and the cosine wave data array from the memory and multiply the read data array by the digital signal to generate one of the second detection signals, a second multiplier configured to sequentially read the other of the sine wave data array and the cosine wave data array from the memory and multiply the read data array by the digital signal to generate the other of the second detection signals, a first analog converter configured to convert the one of the second detection signals to an analog signal, and a second analog converter configured to convert the other of the second detection signals to an analog signal. The reference oscillator may be controlled to change the frequency of the base signal, and an operating frequency of the dual-phase lock-in amplifier is changed to change a readout speed of the sine wave data array and the cosine wave data array from the memory to thereby change the at least one of the frequency and the phase of the second reference signal.

In the above-described signal detection device, the dual-phase lock-in amplifier may further include a first adder configured to add multiplication results output from the first multiplier and average the addition result to generate the one of the second detection signals, and a second adder configured to add multiplication results output from the second multiplier and average the addition result to generate the other of the second detection signals.

In the above-described signal detection device, the second adder may be configured to input the other of the second detection signals into the reference oscillator.

In the above-described signal detection device, the reference oscillator may be configured to change the frequency of the base signal to set the second detection signal input from the second adder to zero.

In the above-described signal detection device, the detector may include a digital converter configured to convert the signal received by the receiver to a digital signal, a storage storing a first data array which includes a sine wave data array or a cosine wave data array to be used as the first reference signal and a second data array which includes a sine wave data array and a cosine wave data array to be used as the second reference signal, and a processor configured to sequentially read the first data array and the second data array from the storage, perform first multiplication of the first data array and the digital signal, second multiplication of the digital signal and the sine wave data array included in the second data array, and third multiplication of the digital signal and the cosine wave data array included in the second data array, and adjust a readout address from the storage according to a multiplication result of the second or third multiplication to change the at least one of the frequency and the phase of each of the first reference signal and the second reference signal.

In the above-described signal detection device, the receiver may include an optical receiver configured to receive at least first light of a first wavelength modulated by the first frequency and second light of a second wavelength modulated by the second frequency to output a signal including the first signal component and the second signal component.

An optical characteristics measurement device that measures optical characteristics of a measurement target according to a second aspect of the present invention may include an illumination device configured to irradiate first light of a first wavelength modulated by a first frequency and second light of a second wavelength modulated by a second frequency to the measurement target, and a signal detection device. The signal detection device may include an optical receiver configured to receive the first light of the first wavelength and the second light of the second wavelength having passed through the measurement target, and a detector configured to generate, using a base signal, a first reference signal to be used for detecting the first light of the first wavelength and a second reference signal to be used for detecting the second light of the second wavelength, perform lock-in detection on a signal of the light received by the optical receiver using the first reference signal to obtain a first detection signal, perform lock-in detection on a signal of the light received by the optical receiver using the second reference signal to obtain two second detection signals having different phases from each other, and change at least one of a frequency and a phase of each of the first and second reference signals to set one of the two second detection signals to zero.

In the above-described optical characteristics measurement device, the detector may include a reference oscillator configured to oscillate the base signal of which the frequency is variable, a divider configured to perform frequency dividing of the base signal to generate the first and second reference signals, a first lock-in amplifier configured to multiply the first reference signal output from the divider by the signal of the light received by the optical receiver to generate the first detection signal, and a second lock-in amplifier configured to multiply the second reference signal output from the divider by the signal of the light received by the optical receiver to generate the two second detection signals. The reference oscillator may be controlled to change the frequency of the base signal to change the at least one of the frequency and the phase of each of the first and second reference signals.

In the above-described optical characteristics measurement device, the second lock-in amplifier may be configured to multiply the second reference signal output from the divider by the signal of the light received by the optical receiver and multiply a third reference signal, which is obtained by shifting the phase of the second reference signal, by the signal of the light received by the optical receiver to generate the two second detection signals having different phases from each other.

In the above-described optical characteristics measurement device, the second lock-in amplifier may be configured to input the second detection signal generated by multiplying the third reference signal by the signal of the light received by the optical receiver into the reference oscillator.

In the above-described optical characteristics measurement device, the reference oscillator may be configured to change the frequency of the base signal to set the second detection signal input from the second lock-in amplifier to zero.

In the above-described optical characteristics measurement device, the detector may include a reference oscillator configured to oscillate the base signal of which the frequency is variable, and a dual-phase lock-in amplifier configured to operate in synchronization with the base signal to generate the second detection signals. The dual-phase lock-in amplifier may include a digital converter configured to convert a signal of the light received by the optical receiver to a digital signal, a memory storing a sine wave data array and a cosine wave data array to be used as the second reference signal, a first multiplier configured to sequentially read one of the sine wave data array and the cosine wave data array from the memory and multiply the read data array by the digital signal to generate one of the second detection signals, a second multiplier configured to sequentially read the other of the sine wave data array and the cosine wave data array from the memory and multiply the read data array by the digital signal to generate the other of the second detection signals, a first analog converter configured to convert the one of the second detection signals to an analog signal, and a second analog converter configured to convert the other of the second detection signals to an analog signal. The reference oscillator may be controlled to change the frequency of the base signal, and an operating frequency of the dual-phase lock-in amplifier is changed to change a readout speed of the sine wave data array and the cosine wave data array from the memory to thereby change the at least one of the frequency and the phase of the second reference signal.

In the above-described optical characteristics measurement device, the detector may include a digital converter configured to convert a signal of the light received by the optical receiver to a digital signal, a storage storing a first data array which includes a sine wave data array or a cosine wave data array to be used as the first reference signal and a second data array which includes a sine wave data array and a cosine wave data array to be used as the second reference signal, and a processor configured to sequentially read the first data array and the second data array from the storage, perform first multiplication of the first data array and the digital signal, second multiplication of the digital signal and the sine wave data array included in the second data array, and third multiplication of the digital signal and the cosine wave data array included in the second data array, and adjust a readout address from the storage according to a multiplication result of the second or third multiplication to change the at least one of the frequency and the phase of each of the first reference signal and the second reference signal.

An optical characteristics measurement device that measures optical characteristics of a measurement target according to a third aspect of the present invention may include an illumination device configured to irradiate first light of a first wavelength modulated by a first frequency and second light of a second wavelength modulated by a second frequency to the measurement target, and a signal detection device. The signal detection device may include an optical receiver configured to receive the first light of the first wavelength and the second light of the second wavelength reflected or scattered by the measurement target, and a detector configured to generate, using a base signal, a first reference signal to be used for detecting the first light of the first wavelength and a second reference signal to be used for detecting the second light of the second wavelength, perform lock-in detection on a signal of the light received by the optical receiver using the first reference signal to obtain a first detection signal, perform lock-in detection on a signal of the light received by the optical receiver using the second reference signal to obtain two second detection signals having different phases from each other, and change at least one of a frequency and a phase of each of the first and second reference signals to set one of the two second detection signals to zero.

According to one aspect of the present invention, a first reference signal to be used for detecting a first signal component and a second reference signal to be used for detecting a second signal component are generated using a base signal, lock-in detection is performed on a signal received by the receiver using the first reference signal to obtain a first detection signal, lock-in detection is performed on the signal received by the receiver using the second reference signal to obtain two second detection signals having different phases, and at least one of a frequency and a phase of each of the first and second reference signal is changed so that at least one of the second detection signals reaches zero. Due to this, a signal detection device is small-sized, lightweight, and inexpensive and can detect a plurality of signals without using a reference signal.

BRIEF DESCRIPTION OF THE DRAWINGS

FIG. 7 is a diagram for describing a data array used in the third embodiment of the present invention.

DETAILED DESCRIPTION OF THE INVENTION

Hereinafter, a signal detection device and an optical characteristics measurement device according to an embodiment of the present invention will be described in detail with reference to the drawings. In order to facilitate understanding, a case in which the optical characteristics measurement device is a moisture meter that measures a moisture content contained in paper will be described as an example. However, it is not intended that the optical characteristics measurement device is limited to a moisture meter, and the optical characteristics measurement device may be an arbitrary device that measures optical characteristics of a measurement target such as a basis weight sensor that measures a weight of paper, for example.

First Embodiment

Figure 1:
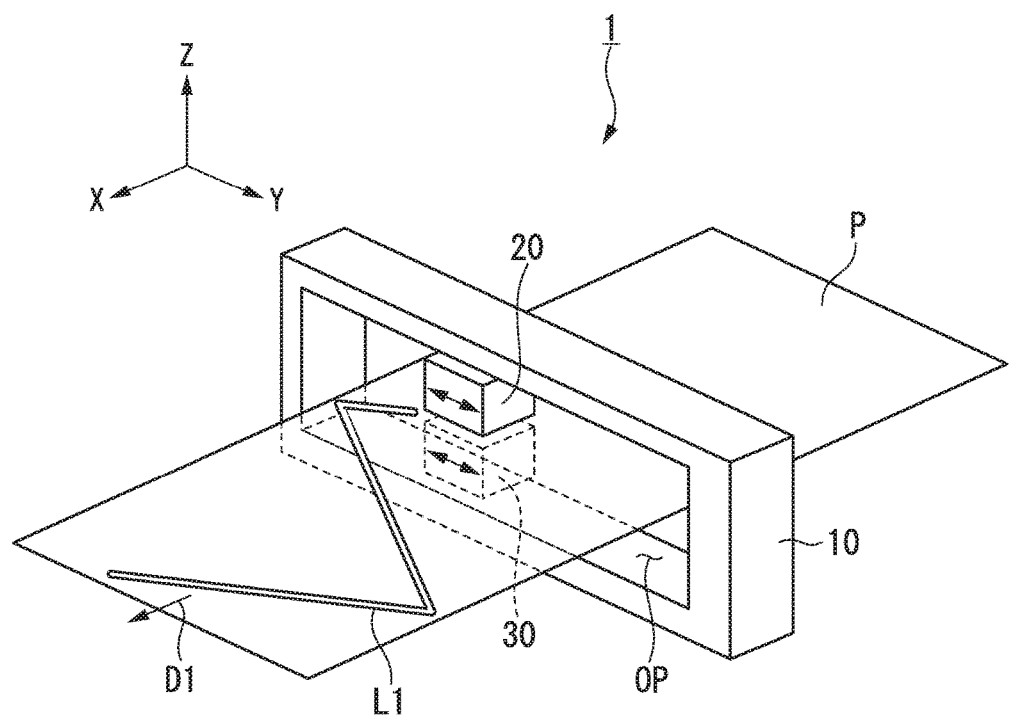
FIG. 1 is a perspective view showing a schematic configuration of a moisture meter as an optical characteristics measurement device according to a first embodiment of the present invention.

FIG. 1 is a perspective view showing a schematic configuration of a moisture meter as an optical characteristics measurement device according to a first embodiment of the present invention. As shown in FIG. 1, a moisture meter 1 includes a frame 10, an upper head 20 (an illumination device), and a lower head 30 (a signal detection device) The moisture meter 1 is attached to a paper machine provided in a paper production plant, for example, to measure a moisture content contained in paper P (a measurement target) produced by the paper machine. In the following description, positional relationships between respective members will be described with reference to an XYZ orthogonal coordinate system set in the drawings as necessary. In the XYZ orthogonal coordinate system shown in FIG. 1, the XYZ axes are set such that the X-axis extends along a conveying direction D1 of the paper P, the Y-axis extends along a width direction of the paper P, and the Z-axis extends in a vertical direction.

The frame 10 is an approximately rectangular annular member of which the outer shape has a longitudinal direction and a lateral direction. The frame 10 is configured such that the upper head 20 and the lower head 30 are supported so as to reciprocate in the longitudinal direction in an opening OP thereof. Specifically, the frame 10 is disposed so that the longitudinal direction thereof extends in the width direction (the Y-direction) of the paper P, the lateral direction thereof extends in the vertical direction (the Z-direction), and the paper P passes through approximately the center of the opening OP.

That is, the frame 10 is positioned in relation to the paper P so that the upper head 20 is disposed on the side above the paper P being conveyed and the lower head 30 is disposed on the side below the paper P being conveyed. Although not shown in FIG. 1, the frame 10 includes a mechanism for allowing the upper head 20 to reciprocate in the Y-direction along an upper surface of the paper P and a mechanism for allowing the lower head 30 to reciprocate in the Y-direction along the rear surface of the paper P. When these mechanisms are driven in the same manner, it is possible to allow the upper head 20 and the lower head 30 to reciprocate in a synchronized manner. When these mechanisms are driven in an independent manner, it is possible to move the upper head 20 and the lower head 30 independently.

As described above, the upper head 20 is supported on the frame 10 so as to be able to reciprocate in the width direction of the paper P along the upper surface of the paper P. The upper head 20 irradiates a plurality of infrared radiations (near-infrared rays) of different wavelengths toward the upper surface of the paper P. Specifically, a near-infrared ray of a wavelength of λ1 (for example, 1.94 μm) having a high absorption ratio in water, a near-infrared ray of a wavelength of 0.2 (for example, 2.1 μm) having a high absorption ratio in cellulose which is a main component of paper, and a near-infrared ray of a wavelength of λ3 (for example, 1.7 μm) having a low absorption ratio in water and cellulose are irradiated to the upper surface of the paper P.

As described above, the lower head 30 is supported on the frame 10 so as to be able to reciprocate in the width direction of the paper P along the rear surface of the paper P. The lower head 30 receives near-infrared rays having passed through the paper P. The moisture content contained in the paper P is measured on the basis of the detection result of the near-infrared rays received by the lower head 30. When the upper head 20 and the lower head 30 are allowed to reciprocate in the width direction (the Y-direction) of the paper P in a synchronized manner with the paper P conveyed in the conveying direction D1 (the X-direction) interposed therebetween, the moisture content contained in the paper P is measured along a zigzag-shaped measurement line L1 shown in FIG. 1.

Figure 2:
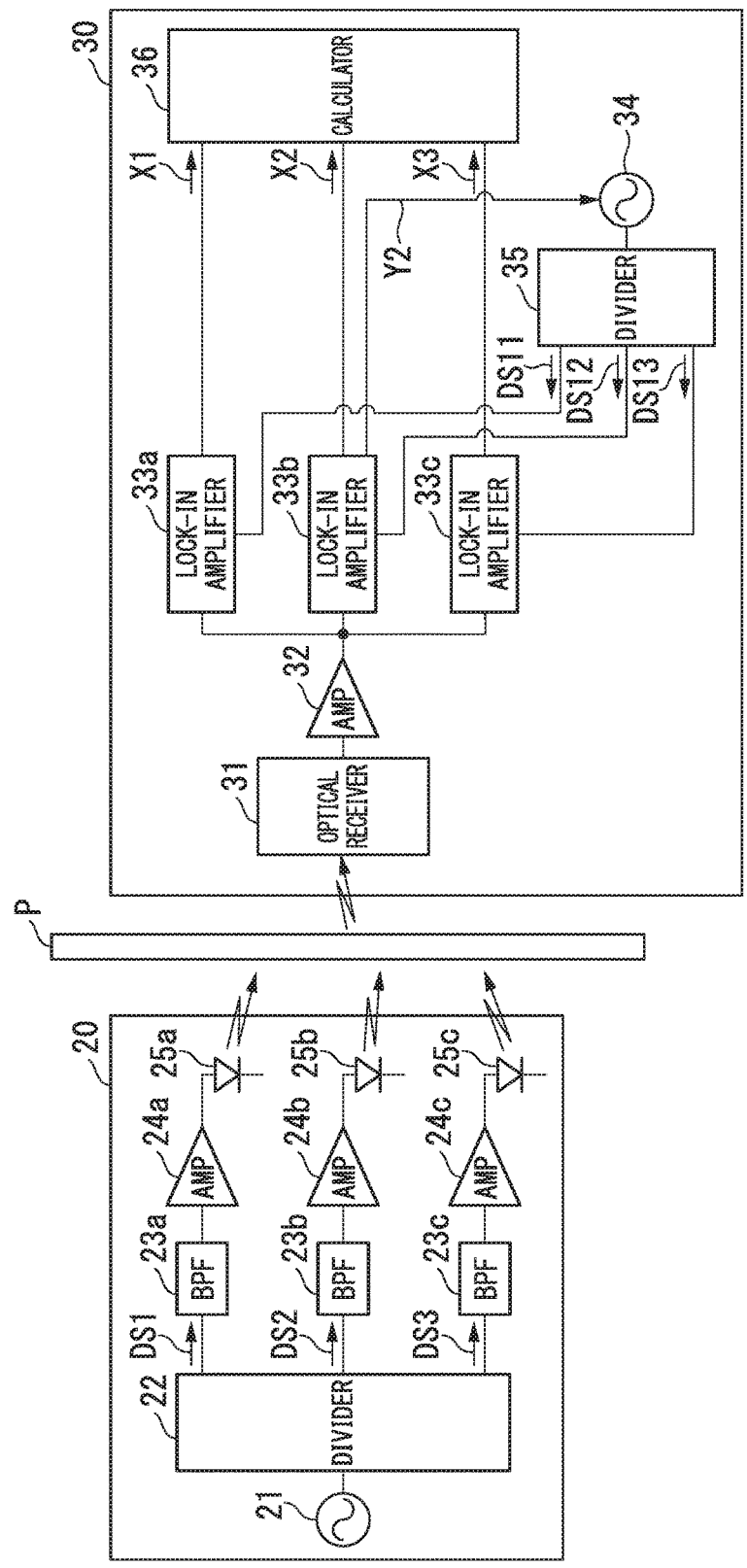
FIG. 2 is a block diagram showing a configuration of main parts of a circuit provided in an upper head and a lower head of the moisture meter as the optical characteristics measurement device according to the first embodiment of the present invention.

FIG. 2 is a block diagram showing a configuration of main parts of a circuit provided in an upper head and a lower head of a moisture meter as an optical characteristics measurement device according to the first embodiment of the present invention. As shown in FIG. 2, a circuit provided in the upper head 20 of the moisture meter 1 includes a reference oscillator 21, a divider 22, band-pass filters (BPFs) 23a to 23c, driving amplifiers (AMPs) 24a to 24c, and light emitters 25a to 25c.

The reference oscillator 21 oscillates a base signal (frequency reference) which is a sine wave having a predetermined frequency (for example, 12 [MHz]). The divider 22 performs frequency dividing of the base signal output from the reference oscillator 21 to output three frequency-division signals DS1 to DS3 having different frequencies. For example, the divider 22 outputs the frequency-division signal DS1 having a frequency of 4 [kHz] to the band-pass filter 23a, outputs the frequency-division signal DS2 having a frequency of 5 [kHz] to the band-pass filter 23b, and outputs the frequency-division signal DS3 having a frequency of 6 [kHz] to the band-pass filter 23c.

The band-pass filters 23a to 23c perform filtering with respect to the frequency-division signals DS1 to DS3 output from the divider 22. These band-pass filters 23a to 23c are provided in order to improve the SN ratios (signal-to-noise ratios) of lock-in amplifiers 33a to 33c to be described later. For example, a passband of the band-pass filter 23a is set such that a central frequency is 4 [kHz] and a bandwidth is approximately several hertz to several tens of hertz [Hz]. A passband of the band-pass filter 23b is set such that a central frequency is 5 [kHz] and a bandwidth is approximately several hertz to several tens of hertz [Hz]. A passband of the band-pass filter 23c is set such that a central frequency is 6 [kHz] and a bandwidth is approximately several hertz to several tens of hertz [Hz].

Therefore, when the passbands are set in the above-described manner, a sinusoidal signal having a frequency of 4 [kHz] is output from the band-pass filter 23a, a sinusoidal signal having a frequency of 5 [kHz] is output from the band-pass filter 23b, and a sinusoidal signal having a frequency of 6 [kHz] is output from the band-pass filter 23c. The driving amplifiers 24a to 24c amplify the signals output from the band-pass filters 23a to 23c by predetermined amplification factors to generate driving signals for driving the light emitters 25a to 25c, respectively.

The light emitters 25a to 25c include, for example, a laser diode (LD) or a light emitting diode (LED). The light emitters 25a to 25c are driven by the driving signals generated by the driving amplifiers 24a to 24c, respectively, such that they emit near-infrared rays which is radiated to the paper P. Specifically, the light emitter 25a emits a near-infrared ray of a wavelength $\lambda 1$ (for example, 1.94 μm) having a high absorption ratio in water, the light emitter 25b emits a near-infrared ray of a wavelength $\lambda 2$ (for example, 2.1 μm) having a high absorption ratio in cellulose, and the light emitter 25c emits a near-infrared ray of a wavelength $\lambda 3$ (for example, 1.7 μm) having a low absorption ratio in water and cellulose. The exemplified LD and LED are elements in which the relation between a driving current and an optical output is nonlinear, and a negative optical output is not present unlike a mathematical sine wave. Therefore, the optical output thereof is controlled such that it is proportional to $\sin \theta + 1$ or $\cos \theta + 1$ using feedback means or offset application means (not shown).

As shown in FIG. 2, the circuit provided in the lower head 30 of the moisture meter 1 includes an optical receiver 31 (a receiver), an amplifier (AMP) 32 (a receiver), lock-in amplifiers 33a to 33c (detectors), a reference oscillator 34 (a detector), a divider 35 (a detector), and a calculator 36. The optical receiver 31 includes a light receiving element such as, for example, a PbS element, a Ge element, or an InGaAs element, that is sensitive to a necessary wavelength region. The optical receiver 31 receives a near-infrared ray having passed through the paper P and outputs an optical signal. The optical signal output from the optical receiver 31 includes a signal component (a first signal component) obtained by receiving the near-infrared ray of the wavelength of 1, a signal component (a second signal component) obtained by receiving the near-infrared ray of the wavelength of $\lambda 2$, and a signal component (a first signal component) obtained by receiving the near-infrared ray of the wavelength of $\lambda 3$. The amplifier 32 amplifies the optical signal output from the optical receiver 31 by a predetermined amplification factor.

The lock-in amplifier 33a (a first lock-in amplifier) performs lock-in detection of the optical signal amplified by the amplifier 32 using a frequency-division signal DS1 output from the divider 35 as a reference signal and detects a signal component of the near-infrared ray of the wavelength of $\lambda 1$ included in the optical signal (specifically, a signal component obtained by receiving the near-infrared ray of the wavelength of $\lambda 1$). The lock-in amplifier 33b (a second lock-in amplifier) performs lock-in detection of the optical signal amplified by the amplifier 32 using a frequency-division signal DS12 output from the divider 35 as a reference signal and detects a signal component of the near-infrared ray of the wavelength of $\lambda 2$ included in the optical signal (specifically, a signal component obtained by receiving the near-infrared ray of the wavelength of $\lambda 2$). The lock-in amplifier 33c (a first lock-in amplifier) performs lock-in detection of the optical signal amplified by the amplifier 32 using a frequency-division signal DS13 output from the divider 35 as a reference signal and detects a signal component of the near-infrared ray of the wavelength of $\lambda 3$ included in the optical signal (specifically, a signal component obtained by receiving the near-infrared ray of the wavelength of $\lambda 3$).

The lock-in amplifiers 33a and 33c detect the signal components of the near-infrared rays of the wavelengths of $\lambda 1$ and $\lambda 3$ and output detection signals $\lambda 1$ and $\lambda 3$ indicating the detection results of performing the lock-in detection. In contrast, the lock-in amplifier 33b performs lock-in detection of the optical signal amplified by the amplifier 32 using a signal obtained by shifting the phase of a frequency-division signal DS12 by 90° as a reference signal in addition to the above-described lock-in detection. In this way, the lock-in amplifier 33b detects the signal component of the near-infrared ray of the wavelength of $\lambda 2$ and outputs two detection signals X2 and Y2 indicating the detection results. Since the detection signals X2 and Y2 output from the lock-in amplifier 33b are signals of which the difference between the phases is 90°, the lock-in amplifier 33b can be referred to as a so-called dual-phase lock-in amplifier.

Such a lock-in amplifier 33b is provided in order to detect a plurality of signal components included in an optical signal without using a reference signal (without receiving the reference signal from the upper head 20). The reason why all lock-in amplifiers 33a to 33c are not configured as dual-phase lock-in amplifiers and the lock-in amplifier 33b only is configured as a dual-phase lock-in amplifier is because it is then possible to prevent an increase in the size, the weight, and the cost of the device as much as possible.

The reference oscillator 34 oscillates a base signal which is a sine wave having a predetermined frequency (for example, 12 [MHz]) similarly to the reference oscillator 21. However, the reference oscillator 34 changes the frequency of the base signal according to the detection signal Y2 output from the lock-in amplifier 33b. Specifically, the reference oscillator 34 includes a voltage controlled xtal (crystal) oscillator (VCXO) and changes the frequency of the base signal so that the value of the detection signal Y2 output from the lock-in amplifier 33b reaches zero. The reason why the frequency of the base signal output from the reference oscillator 34 is varied is to control the frequency and the phase of the base signal output from the reference oscillator 34 such that they are identical to those of the base signal output from the reference oscillator 21.

The divider 35 performs frequency dividing of the base signal output from the reference oscillator 34 to output three frequency-division signals DS11 (a first reference signal), DS12 (a second reference signal), and DS13 (a first reference signal) having different frequencies. The divider 35 has the same configuration as the divider 22 provided in the upper head 20 and outputs frequency-division signals DS11 to DS13 having the same frequencies as the frequencies of the frequency-division signals DS1 to DS3 when a base signal of the same frequency as the frequency of the base signal output from the reference oscillator 21 provided in the upper head 20 is output from the reference oscillator 34. That is, in the above-described case, the divider 35 outputs a frequency-division signal DS11 having a frequency of 4 [kHz], a frequency-division signal DS12 having a frequency of 5 [kHz], and a frequency-division signal DS13 having a frequency of 6 [kHz].

The calculator 36 performs a predetermined arithmetic operation using the detection signals X1 to X3 output from the lock-in amplifiers 33a to 33c and calculates a moisture content contained in the paper P. Specifically, the calculator 36 calculates absorbances for the respective near-infrared rays of the wavelengths λ1 to λ3 on the basis of the detection signals X1 to X3 and performs an arithmetic operation based on the Lambert-Beer law from the obtained absorbances to calculate a weight percent moisture content of cellulose. The information indicating the moisture content calculated by the calculator 36 is displayed on a display (not shown) or output to an external device, for example.

Next, the operation of the moisture meter 1 having the above-described configuration will be described. When the operation of the moisture meter 1 starts, the upper head 20 and the lower head 30 are driven by a mechanism (not shown) provided in the frame 10 and the upper head 20 and the lower head 30 reciprocate in synchronization in the width direction (the Y-direction) of the paper P. Simultaneously with the start of driving of the upper head 20 and the lower head 30, the driving of the light emitters 25a to 25c provided in the upper head 20 starts.

Specifically, when the base signal output from the reference oscillator 21 is input to the divider 22, three frequency-division signals DS1 to DS3 having different frequencies are output from the divider 22. For example, the frequency-division signal DS1 having a frequency of 4 [kHz], the frequency-division signal DS2 having a frequency of 5 [kHz], and the frequency-division signal DS3 having a frequency of 6 [kHz] are output from the divider 22. These frequency-division signals DS1 to DS3 are input to and filtered by the band-pass filters 23a to 23c, respectively.

Signals output from the band-pass filters 23a to 23c are amplified by the driving amplifiers 24a to 24c, respectively. In this way, driving signals for driving the light emitters 25a to 25c are generated. When the driving signals are input to the light emitters 25a to 25c, the light emitters 25a to 25c are driven. By doing this, for example, a near-infrared ray of a wavelength of 1 (for example, 1.94 μm), of which the intensity is modulated at a frequency of 4 [kHz] is emitted from the light emitter 25a. A near-infrared ray of a frequency of 12 (for example, 2.1 μm), of which the intensity is modulated by a frequency of 5 [kHz] is emitted from the light emitter 25b. A near-infrared ray of a wavelength of λ3 (for example, 1.7 μm), of which the intensity is modulated by a frequency of 6 [kHz] is emitted from the light emitter 25c. The exemplified LD and LED are elements in which the relation between a driving current and an optical output is nonlinear, and a negative optical output is not present unlike a mathematical sine wave. Therefore, the optical output thereof is controlled such that it is proportional to sin θ+1 or cos θ+1 using feedback means or offset application means (not shown).

The near-infrared rays emitted from the light emitters 25a to 25c are irradiated to the upper surface of the paper P. Partial portions of the near-infrared rays irradiated to the upper surface of the paper P are reflected, scattered, or absorbed by the paper P, and the remaining portions thereof pass through the paper P. The near-infrared rays having passed through the paper P are received by the optical receiver 31 provided in the lower head 30. The near-infrared ray of the wavelength of λ1 is absorbed by water contained in the paper P when passing through the paper P, and the near-infrared ray of the wavelength of λ2 is absorbed by cellulose which is a main component of the paper P when passing through the paper P. In contrast, the near-infrared ray of the wavelength of λ3 experiences less absorption when passing through the paper P but experiences the same scattering as the near-infrared rays of the wavelengths of λ1 and λ2. Due to this, the intensity of the near-infrared rays of the wavelengths of λ1 and λ2 becomes smaller than the intensity of the near-infrared ray of the wavelength of λ3.

When the near-infrared rays are received by the optical receiver 31, an optical signal is output from the optical receiver 31. This optical signal is amplified by the amplifier 32 and is then input to the lock-in amplifiers 33a to 33c whereby lock-in detection is performed. Specifically, the lock-in amplifier 33a performs a process of multiplying the optical signal amplified by the amplifier 32 by the frequency-division signal DS11 output from the divider 35 to obtain a signal and obtaining the detection signal X1 by removing a high-frequency component of the obtained signal. The lock-in amplifier 33c performs a process of multiplying the optical signal amplified by the amplifier 32 by the frequency-division signal DS13 output from the divider 35 to obtain a signal and obtaining the detection signal X3 by removing a high-frequency component of the obtained signal.

The lock-in amplifier 33b performs a process of multiplying the optical signal amplified by the amplifier 32 by the frequency-division signal DS12 output from the divider 35 to obtain a signal and obtaining the detection signal X2 by removing a high-frequency component of the obtained signal. Furthermore, the lock-in amplifier 33b performs a process of multiplying the optical signal amplified by the amplifier 32 by a signal obtained by shifting the phase of the frequency-division signal DS12 by 90° to obtain a signal and obtaining the detection signal Y2 by removing a high-frequency component from the obtained signal.

The detection signal Y2 output from the lock-in amplifier 33b is input to the reference oscillator 34. The reference oscillator 34 performs control of changing the frequency of the base signal so that the value of the detection signal Y2 output from the lock-in amplifier 33b reaches zero. When the frequency of the base signal changes, the frequencies of the frequency-division signals DS11 to DS13 output from the divider 35 also change by amounts according to the amount of change in the frequency of the base signal. In this way, the lock-in amplifiers 33a to 33c perform lock-in detection using the frequency-division signals DS11 to DS13 of which the frequencies are changed as reference signals, respectively.

When such an operation is repeated and the value of the detection signal Y2 output from the lock-in amplifier 33b reaches zero, the frequency and the phase of the base signal output from the reference oscillator 34 become identical to those of the base signal output from the reference oscillator 21. By doing so, the frequencies and the phases of the frequency-division signals DS11 to DS13 output from the divider 35 are identical to the frequencies and the phases of the frequency-division signals DS1 to DS3 output from the divider 22.

After that, the lock-in amplifier 33a performs lock-in detection using the frequency-division signal DS11 of which the frequency and the phase are identical to those of the frequency-division signal DS1 output from the divider 22 as a reference signal. The lock-in amplifier 33b performs lock-in detection using the frequency-division signal DS12 of which the frequency and the phase are identical to those of the frequency-division signal DS2 output from the divider 22 as a reference signal. The lock-in amplifier 33c performs lock-in detection using the frequency-division signal DS13 of which the frequency and the phase are identical to those of the frequency-division signal DS3 output from the divider 22 as a reference signal. In this way, variations of the detection signals X1 to X3 are prevented.

The detection signals X1 to X3 output from the lock-in amplifiers 33a to 33c are input to the calculator 36. Moreover, the calculator 36 performs a process of calculating the absorbances of the near-infrared rays of the wavelengths of λ1 to λ3 on the basis of the input detection signals X1 to X3, performs an arithmetic operation based on the Lambert-Beer law from the obtained absorbances, and performs a process of calculating a weight percent moisture content of cellulose. The information indicating the moisture content calculated by the calculator 36 is displayed on a display (not shown) or output to an external device, for example.

As described above, in the present embodiment, the reference oscillator 34 capable of outputting a base signal having the same frequency as the reference oscillator 21 provided in the upper head 20, the divider 35 having the same configuration as the divider 22 provided in the upper head 20, and the lock-in amplifier 33b as a dual-phase lock-in amplifier are provided in the lower head 30. Moreover, the frequencies of the frequency-division signals DS11 to DS13 used as the reference signals of the lock-in amplifiers 33a to 33c are changed by controlling the reference oscillator 34 such that it changes the frequencies of the base signals so that the detection signal Y2 output from the lock-in amplifier 33b reaches zero.

Due to this, even when a reference signal is not transferred from the upper head 20 to the lower head 30, it is possible to detect a plurality of signal components (the detection signals X1 to X3) included in the optical signal output from the optical receiver 31 with high accuracy. Since all lock-in amplifiers 33a to 33c are not configured as dual-phase lock-in amplifiers and the lock-in amplifier 33b only is configured as a dual-phase lock-in amplifier, it is possible to realize a small-size, lightweight, and low-cost device without increasing the size, the weight, and the cost.

Second Embodiment

Figures 3, 4:
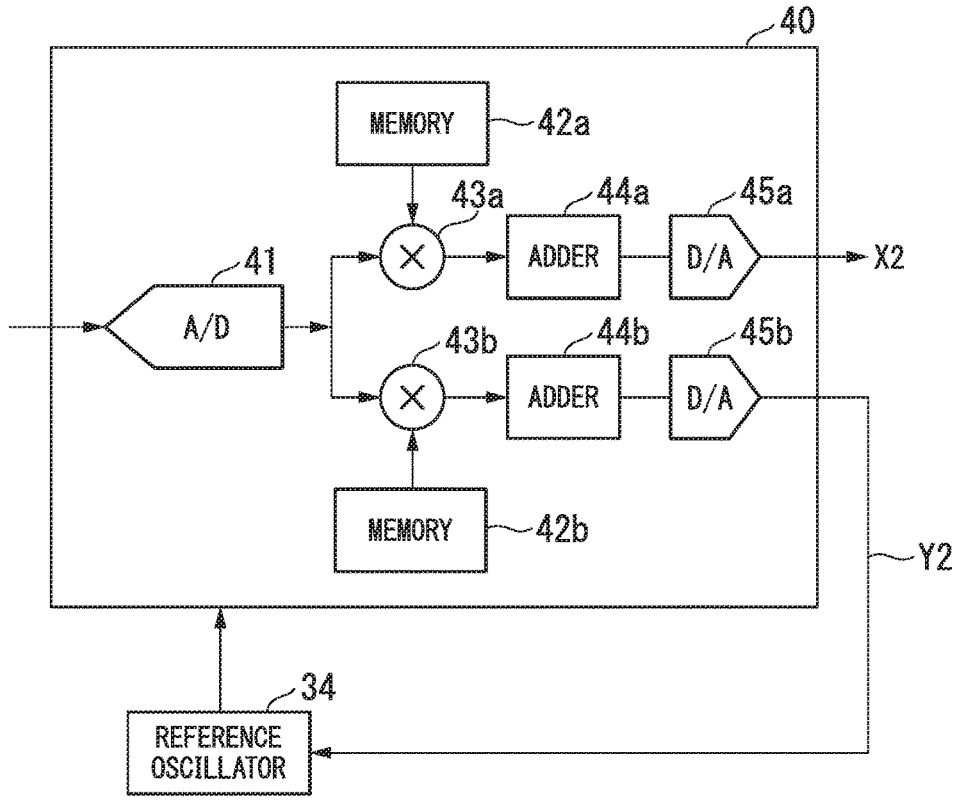
FIG. 3 is a block diagram showing a configuration of a dual-phase lock-in amplifier provided in a lower head according to a second embodiment of the present invention.
FIG. 4 is a diagram for describing a cosine wave data array and a sine wave data array used in the second embodiment of the present invention.

Next, a second embodiment of the present invention will be described in detail. A moisture meter 1 as an optical characteristics measurement device of the present embodiment has a configuration in which the lock-in amplifier 33b (see FIG. 2) provided in the lower head 30 is replaced with a lock-in amplifier 40 shown in FIG. 3. FIG. 3 is a block diagram showing a configuration of a dual-phase lock-in amplifier provided in a lower head according to a second embodiment of the present invention. In the present embodiment, as shown in FIG. 3, since the base signal (frequency reference) output from the reference oscillator 34 is input directly to the lock-in amplifier 40, the frequency-division signal DS12 output from the divider 35 is not used.

As shown in FIG. 3, the lock-in amplifier 40 (a dual-phase lock-in amplifier) includes an A/D converter 41 (a digital converter), memories 42a and 42b, multipliers 43a and 43b (first and second multipliers), adders 44a and 44b, and D/A converters 45a and 45b (first and second analog converters) and operates in synchronization with the base signal output from the reference oscillator 34. Although the lock-in amplifier 33b that processes digital signals is described in the present embodiment as an example, the lock-in amplifier 33b may process analog signals.

The A/D converter 41 converts the optical signal amplified by the amplifier 32 to a digital signal. Specifically, the A/D converter 41 samples the optical signal amplified by the amplifier 32 to convert the optical signal to a digital signal in synchronization with the base signal output from the reference oscillator 34. A sampling frequency of the A/D converter 41 is 256 [kHz], for example. The memories 42a and 42b store a data array of a reference signal necessary for performing lock-in detection. Specifically, the memory 42a stores a cosine wave data array and the memory 42b stores a sine wave data array.

FIG. 4 is a diagram for describing a cosine wave data array and a sine wave data array used in the second embodiment of the present invention. As shown in FIG. 4, a cosine wave data array M(i) is a data array made up of 256 items of data which are obtained by dividing five cycles of a cosine wave into 256 parts and arranging the values (the cosine values) at the respective division points in the order of division points. A sine wave data array N(i) is a data array made up of 256 items of data which are obtained by dividing five cycles of a sine wave into 256 parts and arranging the values (the sine values) at the respective division points in the order of division points. The cosine wave data array M(i) is stored in the order from address [0] to address [255] of the memory 42a, and the sine wave data array N(i) is stored in the order from address [0] to [255] of the memory 42b.

The following is the reason why five cycles of the cosine wave data array M(i) and the sine wave data array N(i) are stored in the memories 42a and 42b, respectively. That is, the lock-in amplifier 33b used in the first embodiment performs lock-in detection of the optical signal using the frequency-division signal DS12 having the frequency of 5 [kHz] as a reference signal to detect a signal component of the near-infrared ray of the wavelength of λ2 included in the optical signal (specifically, a signal component obtained by receiving the near-infrared ray of the wavelength of λ2 of which the intensity is modulated by the frequency of 5 [kHz]). The lock-in amplifier 40 stores five cycles of the cosine wave data array M(i) and the sine wave data array N(i) in the memories 42a and 42b in order to obtain the same signal as the frequency-division signal DS12 used as the reference signal by the lock-in amplifier 33b.

In FIG. 4, in order to facilitate understanding, the cosine wave data array M(i) is the cosine values as they are and the sine wave data array N(i) is the sine values as they are. In order to facilitate digital processing, the cosine and sine values are multiplied by a coefficient (for example, 65535), an offset (for example, 32768) being added to the multiplication results to obtain 16-bit positive integer values which may be used as the cosine wave data array M(i) and the sine wave data array N(i), respectively.

The multiplier 43a multiplies sequentially the digital signal sequentially output from the A/D converter 41 by the cosine wave data sequentially read from the memory 42a. The multiplier 43b multiplies sequentially the digital signal sequentially output from the A/D converter 41 by the sine wave data sequentially read from the memory 42b. The readout frequency of the cosine wave data and the sine wave data of the multipliers 43a and 43b is 256 [kHz], for example.

The adder 44a performs a process of adding a predetermined number (for example, 256) of multiplication results obtained by the multiplier 43a to obtain an average value thereof. The adder 44b performs a process of adding a predetermined number (for example, 256) of multiplication results obtained by the multiplier 43b to obtain an average value thereof. The D/A converters 45a and 45b perform a process of converting the average values calculated by the adders 44a and 44b to analog signals. The operating frequency of the lock-in amplifier 40 is 256 [kHz], for example, when a base signal having the same frequency as the frequency of the base signal output from the reference oscillator 21 provided in the upper head 20 is output from the reference oscillator 34.

Next, the operation of the moisture meter 1 having the above-described configuration will be described. Operations other than those of the lock-in amplifier 40 are basically the same as those of the first embodiment. Due to this, the operation of the lock-in amplifier 40 will be mainly described below. When the operation of the moisture meter 1 starts, an operation similar to the operation described in the first embodiment is performed and the near-infrared rays emitted from the light emitters 25a to 25c are irradiated to the upper surface of the paper P.

Partial portions of the near-infrared rays irradiated to the upper surface of the paper P are reflected, scattered, or absorbed by the paper P, and the remaining portions thereof pass through the paper P. The near-infrared rays having passed through the paper P are received by the optical receiver 31 provided in the lower head 30. When the near-infrared rays are received by the optical receiver 31, an optical signal is output from the optical receiver 31. This optical signal is amplified by the amplifier 32 and is then input to the lock-in amplifiers 33a and 33b and the lock-in amplifier 40 whereby lock-in detection is performed.

Figure 5:
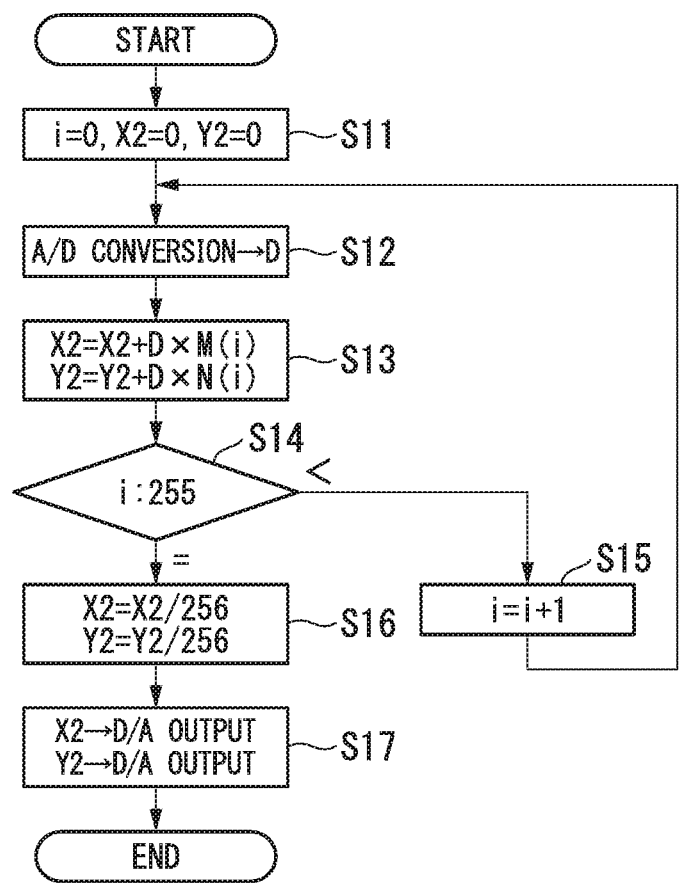
FIG. 5 is a flowchart showing processing performed by a dual-phase lock-in amplifier provided in a lower head according to the second embodiment of the present invention.

The lock-in amplifiers 33a and 33c perform a process similar to the process described in the first embodiment and the detection signals X1 and X3 are obtained, respectively. In contrast, the lock-in amplifier 40 performs a process shown in FIG. 5. FIG. 5 is a flowchart showing processing performed by the dual-phase lock-in amplifier provided in the lower head according to the second embodiment of the present invention. The processing of the flowchart shown in FIG. 5 is performed repeatedly at predetermined intervals (for example, 1 [msec]).

When the processing of the flowchart shown in FIG. 5 starts, first, an initialization process is performed (step S11). Specifically, a process of initializing an address i used for reading the cosine wave data array M(i) and the sine wave data array N(i) from the memories 42a and 42b (the value is set to "0") and initializing the adders 44a and 44b (the values are set to "0") to set the output (the detection signals λ2 and Y2) of the lock-in amplifier 40 to "0" is performed.

Subsequently, the operation of the A/D converter 41 starts and a process of sampling the optical signal (the optical signal amplified by the amplifier 32) and converting the optical signal to a digital signal is performed (step S12). In FIG. 5, the optical signal converted to a digital signal is represented by "D". The optical signal converted to the digital signal by the A/D converter 41 is input to the multipliers 43a and 43b.

Moreover, the multiplier 43a performs a process of multiplying the optical signal converted to the digital signal by the cosine wave data array M(i) stored in the address i of the memory 42a. The multiplier 43b performs a process of multiplying the optical signal converted to the digital signal with the sine wave data array N(i) stored in the address i of the memory 42b. In FIG. 5, the process performed by the multiplier 43a is represented by "D×M(i)", and the process performed by the multiplier 43b is represented by "D×N(i)". The multiplication result of the multiplier 43a is output to the adder 44a and is added to a previous value (in this example, "0"), and the multiplication result of the multiplier 43b is output to the adder 44b and is added to a previous value (in this example, "0") (step S13).

Subsequently, the address "i" is compared with "255" which is a largest value of the address (step S14). When the address i is smaller than the value "255" (i<255), the address i is incremented (step S15), and a process of sampling the optical signal (the optical signal amplified by the amplifier 32) and converting the optical signal to a digital signal is performed again (step S12). The processes of steps S12 to S15 are performed repeatedly during a period in which the address i is smaller than the value "255" (i<255).

In contrast, when the address i is equal to the value "255" (i=255), the adder 44a performs a process of averaging the detection signal X2 and the adder 44b performs a process of averaging the detection signal Y2 (step S16). When this averaging process is performed, the averaged detection signal X2 is output from the adder 44a and is converted to an analog signal by the D/A converter 45a, and the averaged detection signal Y2 is output from the adder 44b and is converted to an analog signal by the D/A converter 45b (step S17). In this way, a series of processes ends. As described above, the processing of the flowchart shown in FIG. 5 is performed repeatedly at a predetermined cycle (for example, 1 [msec]).

The detection signal Y2 of the analog signal output from the lock-in amplifier 40 is input to the reference oscillator 34. The reference oscillator 34 performs control of changing the frequency of the base signal so that the value of the detection signal Y2 output from the lock-in amplifier 40 reaches zero. When the frequency of the base signal changes, the operation speed of the lock-in amplifier 40 changes and the readout speed of the cosine wave data array M(i) from the memory 42a and the readout speed of the sine wave data array N(i) from the memory 42b change. In this way, the frequency of the reference signal used by the lock-in amplifier 40 changes. When the above-described control is performed and the frequency of the base signal changes, the frequencies and the phases of the frequency-division signals DS11 and DS13 (the reference signals used by the lock-in amplifiers 33a and 33c) output from the divider 35 shown in FIG. 2 change.

When such an operation is repeated and the value of the detection signal Y2 output from the lock-in amplifier 40 reaches zero, the frequency and the phase of the base signal output from the reference oscillator 34 are identical to those of the base signal output from the reference oscillator 21. In this way, in the lock-in amplifier 40, the cosine wave data array M(i) of which the frequency and the phase are identical to those of the frequency-division signal DS2 output from the divider 22 is read from the memory 42a, and the sine wave data array N(i) of which the frequency is identical to the frequency-division signal DS2 but the phase is shifted by 90° from that of the frequency-division signal DS2 is read from the memory 42b. In this way, the lock-in amplifier 40 performs lock-in detection using a reference signal (the cosine wave data array M(i)) of which the frequency and the phase are identical to those of the frequency-division signal DS2 output from the divider 22.

When the frequency and the phase of the base signal output from the reference oscillator 21 are identical to those of the base signal output from the reference oscillator 34, the frequencies and the phases of the frequency-division signals DS11 and DS13 output from the divider 35 are identical to those of the frequency-division signals DS1 and DS3 output from the divider 22, respectively. Due to this, the lock-in amplifier 33a performs lock-in detection using the frequency-division signal DS11 of which the frequency and the phase are identical to those of the frequency-division signal DS1 output from the divider 22 as a reference signal, and the lock-in amplifier 33c performs lock-in detection using the frequency-division signal DS13 of which the frequency and the phase are identical to those of the frequency-division signal DS3 output from the divider 22 as a reference signal. In this way, variations of the detection signals X1 to X3 are prevented.

As described above, in the present embodiment, the reference oscillator 34 capable of outputting a base signal having the same frequency as the reference oscillator 21 provided in the upper head 20 and the lock-in amplifier 40 as a dual-phase lock-in amplifier are provided in the lower head 30. Moreover, the readout speed of the cosine wave data array M(i) and the sine wave data array N(i) in the lock-in amplifier 40 is changed to change the frequency of the reference signal by controlling the reference oscillator 34 to change the frequency of the base signal so that the detection signal Y2 output from the lock-in amplifier 40 reaches zero. In the lock-in amplifiers 33a and 33c, the frequencies of the frequency-division signals DS11 and DS13 used as the reference signals are changed.

Due to this, even when a reference signal is not transferred from the upper head 20 to the lower head 30, it is possible to detect a plurality of signal components (the detection signals X1 to X3) included in the optical signal output from the optical receiver 31 with high accuracy. In the present embodiment, since the lock-in amplifier 33b shown in FIG. 2 is replaced with the lock-in amplifier 40, it is possible to realize a small-size, lightweight, and low-cost device without increasing the size, the weight, and the cost similarly to the first embodiment.

Third Embodiment

Figure 6:
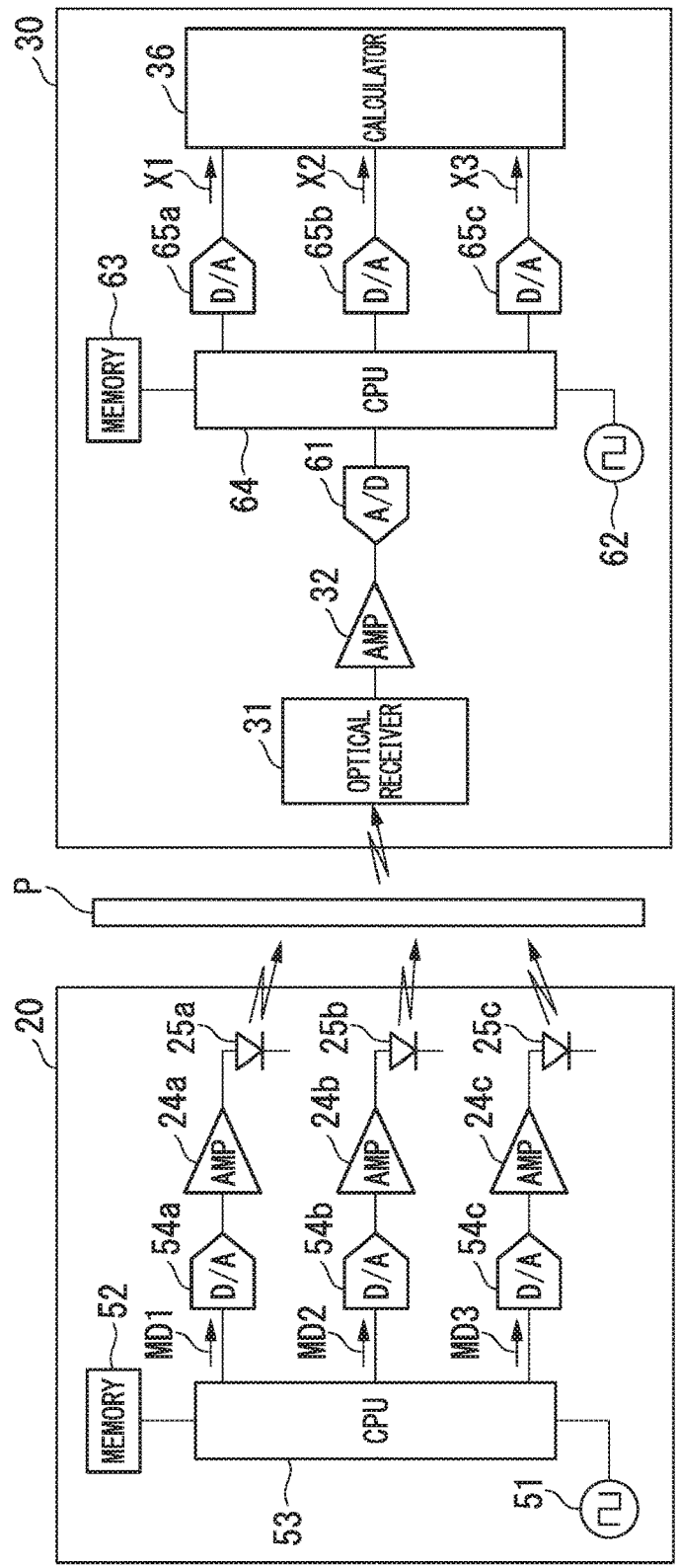
FIG. 6 is a block diagram showing a configuration of main parts of a circuit provided in an upper head and a lower head of a moisture meter as an optical characteristics measurement device according to a third embodiment of the present invention.

FIG. 6 is a block diagram showing a configuration of main parts of a circuit provided in an upper head and a lower head of a moisture meter as an optical characteristics measurement device according to a third embodiment of the present invention. In FIG. 6, constituent elements the same as those shown in FIG. 2 are denoted by the same reference numerals. The moisture meter 1 of the present embodiment has a configuration in which the circuit provided in the upper head and the lower head is configured as a digital circuit.

As shown in FIG. 6, the circuit provided in the upper head 20 of the moisture meter 1 includes a reference oscillator 51, a memory 52, a central processing unit (CPU) 53, D/A converters 54a to 54c, and the driving amplifiers 24a to 24c and the light emitters 25a to 25c shown in FIG. 2. The reference oscillator 51 oscillates a base signal (frequency reference) which is a rectangular wave having a predetermined frequency (for example, 12 [MHz]). The memory 52 stores a data array necessary for modulating the intensity of near-infrared rays emitted from the light emitters 25a to 25c.

Specifically, the memory 52 stores three data arrays L(i), M(i), and P(i). The data array L(i) is a data array necessary for modulating the intensity of the near-infrared ray of the wavelength of λ1 emitted from the light emitter 25a by the frequency of 4 [kHz]. The data array M(i) is a data array necessary for modulating the intensity of the near-infrared ray of the wavelength of λ2 emitted from the light emitter 25b by the frequency of 5 [kHz]. The data array P(i) is a data array necessary for modulating the intensity of the near-infrared ray of the wavelength of λ3 emitted from the light emitter 25c by the frequency of 6 [kHz].

FIG. 7 is a diagram for describing a data array used in the third embodiment of the present invention. As shown in FIG. 7, the data array L(i) is a data array made up of 256 items of data which are obtained by dividing four cycles of a cosine wave into 256 parts and arranging the values (the cosine values) at the respective division points in the order of division points. The data array M(i) is the same data array as the cosine wave data array M(i) shown in FIG. 4 and is a data array made up of 256 items of data which are obtained by dividing five cycles of a cosine wave into 256 parts and arranging the values (the cosine values) at the respective division points in the order of division points. The data array P(i) is a data array made up of 256 items of data which are obtained by dividing six cycles of a cosine wave into 256 parts and arranging the values (the cosine values) at the respective division points in the order of division points.

The reason why the data array L(i) for four cycles of a cosine wave is stored in the memory 52 is to modulate the intensity of the near-infrared ray of the wavelength of λ1 by the frequency of 4 [kHz]. The reason why the data array M(i) for five cycles of a cosine wave is stored in the memory 52 is to modulate the intensity of the near-infrared ray of the wavelength of λ2 by the frequency of 5 [kHz]. The reason why the data array P(i) for six cycles of a cosine wave is stored in the memory 52 is to modulate the intensity of the near-infrared ray of the wavelength of λ3 by the frequency of 6 [kHz].

In FIG. 7, for the same reason as in FIG. 4, the data arrays L(i), M(i), and P(i) are the cosine values as they are and the data array N(i) is the sine values as they are. In order to facilitate digital processing, a coefficient (for example, 65535) is multiplied with the cosine and sine values, an offset (for example, 32768) being added to the multiplication results to obtain 16-bit positive integer values which may be used as the data arrays L(i), M(i), N(i), and P(i), respectively.

The CPU 53 operates in synchronization with the base signal output from the reference oscillator 51 and outputs modulation signals MD1 to MD3 for modulating the intensity of the near-infrared rays emitted from the light emitters 25a to 25c, respectively. Specifically, the CPU 53 sequentially reads the data arrays L(i), M(i), and P(i) from the memory 52 in synchronization with the base signal output from the reference oscillator 51 and sequentially outputs the read data arrays L(i), M(i), and P(i) to the D/A converters 54a to 54c as the modulation signals MD1 to MD3 in synchronization with the base signal output from the reference oscillator 51. The frequency in which the CPU 53 reads the data arrays L(i), M(i), and P(i) from the memory 52 for the cycle in which the CPU 53 outputs the modulation signals MD1 to MD3 is 256 [kHz], for example. The D/A converters 54a to 54c convert the modulation signals MD1 to MD3 output from the CPU 53 to analog signals and output the analog signals to the driving amplifiers 24a to 24c, respectively.

As shown in FIG. 6, the circuit provided in the lower head 30 of the moisture meter 1 includes the optical receiver 31, the amplifier 32, and the calculator 36 shown in FIG. 2, an A/D converter 61 (a digital converter), a reference oscillator 62, a memory 63 (a storage), a CPU 64 (a processor), and D/A converters 65a to 65c. The A/D converter 61 converts the optical signal amplified by the amplifier 32 to a digital signal. The reference oscillator 62 oscillates a base signal which is a rectangular wave having a predetermined frequency (for example, 12 [MHz]) similarly to the reference oscillator 51.

The memory 63 stores a data array of a reference signal necessary for performing lock-in detection. Specifically, the memory 63 stores four data arrays L(i), M(i). N(i), and P(i) shown in FIG. 7. The data arrays L(i), M(i), and P(i) are the same as the data arrays L(i), M(i), and P(i) stored in the memory 52 of the upper head 20. The data array N(i) is the same data array as the sine wave data array N(i) shown in FIG. 4 and is a data array made up of 256 items of data which are obtained by dividing five cycles of a sine wave into 256 parts and arranging the values (the sine values) at the respective division points in the order of division points.

This data array N(i) is used for performing lock-in detection to obtain the detection signal Y2 similarly to the second embodiment.

The CPU 64 operates in synchronization with the base signal output from the reference oscillator 62 and performs lock-in detection of a signal output from the A/D converter 61 using the data arrays L(i), M(i), N(i), and P(i) stored in the memory 63. Specifically, the CPU 64 individually multiplies the digital signals sequentially output from the A/D converter 61 and the four data arrays L(i), M(i), N(i), and P(i) sequentially read from the memory 42a.

The CPU 64 performs a process of individually adding a predetermined number (for example, 256) of multiplication results to obtain an average value thereof. Moreover, the CPU 64 outputs the average value obtained using the data array L(i) to the D/A converter 65a, outputs the average value obtained using the data array M(i) to the D/A converter 65b, and outputs the average value obtained using the data array P(i) to the D/A converter 65c.

The CPU 64 performs a process of adjusting a readout address of the memory 63 according to an average value (a value corresponding to the detection signal Y2) obtained using the data array N(i). Such a process is performed so as to change at least one of the frequency and the phase of the reference signal used for performing lock-in detection of the signal output from the A/D converter 61. The frequency in which the CPU 64 reads the data arrays L(i), M(i), N(i), and P(i) from the memory 63 and the frequency in which the CPU 64 outputs the average value are 1 [kHz], for example. The D/A converters 65a to 65c convert the average value output from the CPU 64 to an analog signal.

Figure 8:
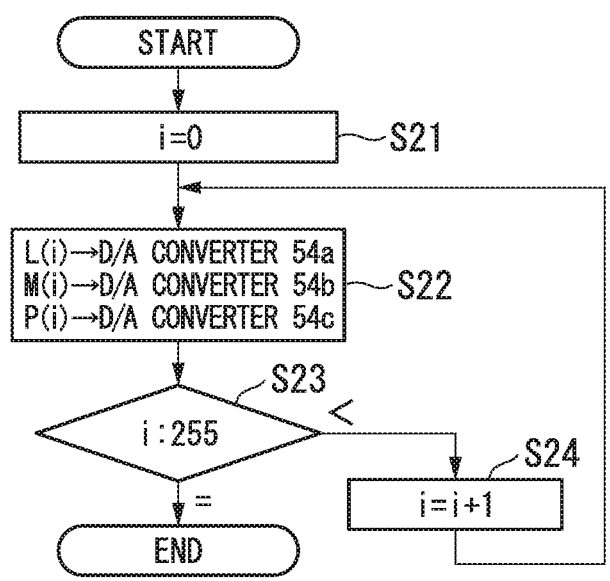
FIG. 8 is a flowchart showing processing performed by an upper head according to the third embodiment of the present invention.

Next, an operation of the moisture meter 1 having the above-described configuration will be described. When the operation of the moisture meter 1 starts and the driving of the upper head 20 and the lower head 30 (synchronized driving in the width direction (Y-direction) of the paper P) starts, the processing of the flowchart shown in FIG. 8 is performed and the driving of the light emitters 25a to 25c provided in the upper head 20 also starts. FIG. 8 is a flowchart showing the processing performed by the upper head according to the third embodiment of the present invention. The processing of the flowchart shown in FIG. 8 is performed repeatedly at a predetermined cycle (for example, 1/256 [msec]).

When the processing of the flowchart shown in FIG. 8 starts, first, an initialization process is performed (step S21). Specifically, a process of initializing the address i used for reading the data arrays L(i), M(i), and P(i) from the memory 52 (the value is set to "0") is performed. When the initialization process ends, the CPU 53 performs a process of reading the data arrays L(i), M(i), and P(i) from the memory 52 one by one in synchronization with the base signal output from the reference oscillator 51 and outputting the read data arrays L(i), M(i), and P(i) to the D/A converters 54a to 54c, respectively, as the modulation signals MD1 to MD3 in synchronization with the base signal output from the reference oscillator 51 (step S22).

Subsequently, the address "i" is compared with "255" which is a largest value of the address (step S23). When the address i is smaller than the value "255" (i<255), a process of incrementing the address i is performed (step S24), and the CPU 53 performs a process of reading the data arrays L(i), M(i), and P(i) one by one from the memory 52 and outputting the read data arrays L(i). M(i), and P(i) to the D/A converters 54a to 54c, respectively, again (step S22).

The processes of steps S22 to S24 are performed repeatedly during a period in which the address i is smaller than the value "255" (i<255). In contrast, when the address i is equal to the value "255" (i=255), a series of processes shown in FIG. 8 end. As described above, the processing of the flowchart shown in FIG. 8 is performed repeatedly at a predetermined cycle (for example, 1 [msec]).

The modulation signals MD1 to MD3 output from the CPU 53 are converted to analog signals by the D/A converters 54a to 54c, respectively, and are then amplified by the driving amplifiers 24a to 24c, respectively. In this way, driving signals for driving the light emitters 25a to 25c are generated. When the driving signals are input to the light emitters 25a to 25c, the light emitters 25a to 25c are driven. By doing so, for example, a near-infrared ray of a wavelength of λ1 (for example, 1.94 μm), of which the intensity is modulated by a frequency of 4 [kHz] is emitted from the light emitter 25a, a near-infrared ray of a wavelength of λ2 (for example, 2.1 μm), of which the intensity is modulated by a frequency of 5 [kHz] is emitted from the light emitter 25b, and a near-infrared ray of a wavelength of λ3 (for example, 1.7 μm), of which the intensity is modulated by a frequency of 6 [kHz] is emitted from the light emitter 25c. Moreover, the near-infrared rays are irradiated to the upper surface of the paper P.

Partial portions of the near-infrared rays irradiated to the upper surface of the paper P are reflected, scattered, or absorbed by the paper P, and the remaining portions thereof pass through the paper P. The near-infrared rays having passed through the paper P are received by the optical receiver 31 provided in the lower head 30. When the near-infrared rays are received by the optical receiver 31, an optical signal is output from the optical receiver 31. This optical signal is amplified by the amplifier 32 and is converted to a digital signal by the A/D converter 61, and is then input to the CPU 64, and lock-in detection is performed by the process shown in FIG. 9.

Figure 9:
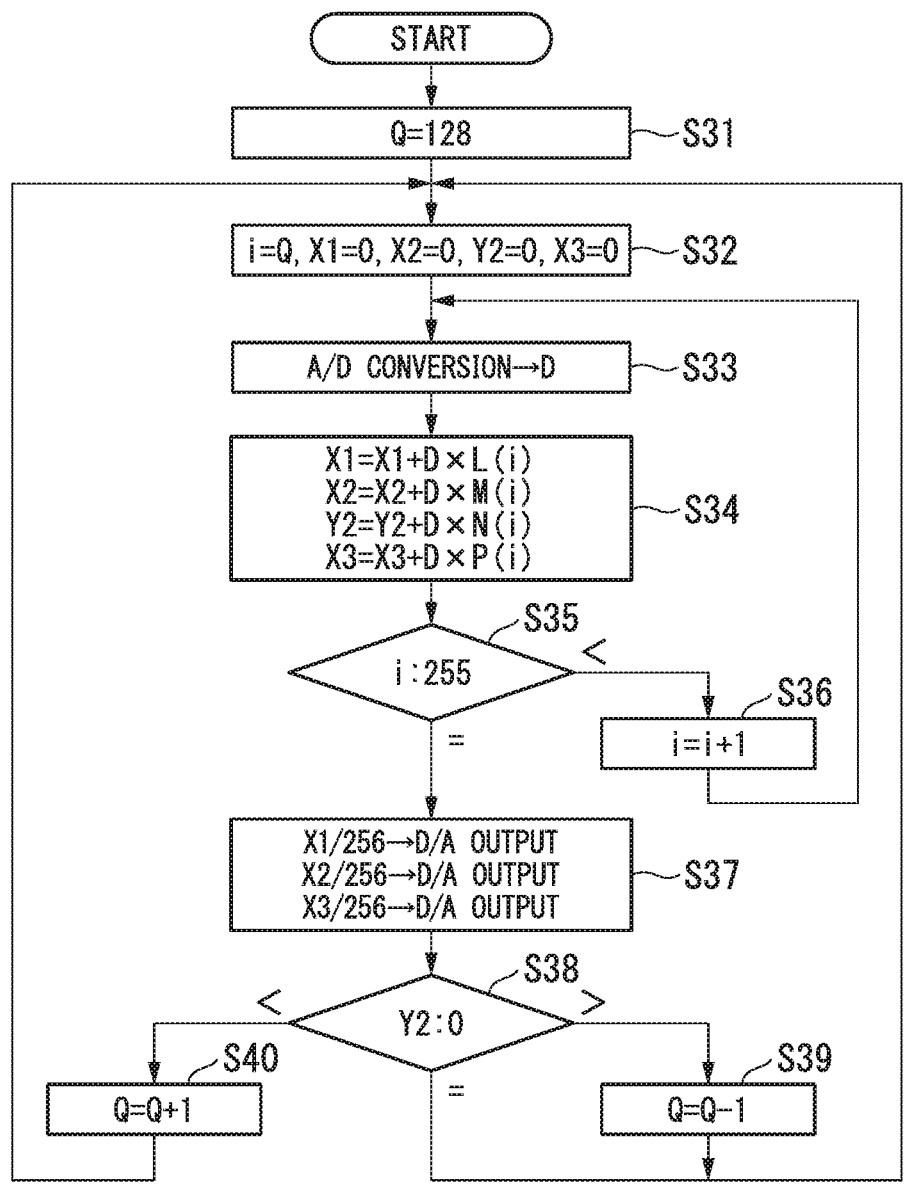
FIG. 9 is a flowchart showing processing performed by a CPU provided in a lower head according to the third embodiment of the present invention.

FIG. 9 is a flowchart showing the processing performed by a CPU provided in the lower head according to the third embodiment of the present invention. When the processing of the flowchart shown in FIG. 9 starts, first, a process of setting an initial value Q of a readout address of the memory 63 is performed (step S31). For example, a process of setting the initial value Q of the readout address to "128" is performed.

Subsequently, an initialization process is performed (step S32). Specifically, a process of setting the initial value Q of the address to the address i used for reading the data arrays L(i), M(i), N(i), and P(i) from the memory 63 and initializing the detection signals X1, X2, Y2, and λ3 (the values are set to "0") is performed. Subsequently, the operation of the A/D converter 61 starts, and a process of sampling the optical signal (the optical signal amplified by the amplifier 32) to convert the optical signal to a digital signal is performed (step S33). In FIG. 9, the optical signal converted to the digital signal is represented by "D" similarly to FIG. 5. The optical signal converted to the digital signal by the A/D converter 61 is input to the CPU 64.

By doing so, the CPU 64 performs a process of individually multiplying the optical signal converted to the digital signal with the data arrays L(i), M(i), N(i), and P(i) stored in the address i of the memory 63 and individually adding the respective multiplication results to the previous values (in this example, "0") (step S34). In FIG. 9, these processes are represented by "X1=X1+D×L(i)", "X2=X2+D×M(i)", "Y2=Y2+D×N(i)", and "X3=X3+D×P(i)".

Subsequently, the address i is compared with "255" which is a largest value of the address (step S35). When the address i is smaller than the value "255" (i<255), a process of incrementing the address i is performed (step S36), and a process of sampling the optical signal (the optical signal amplified by the amplifier 32) and converting the optical signal to a digital signal is performed again (step S33). The processes of steps S33 to S36 are performed repeatedly during a period in which the address i is smaller than the value "255" (i<255). In contrast, when the address i is equal to the value "255" (i=255), the CPU 64 performs a process of individually averaging the detection signals X1, X2, and X3 and outputting the same to the D/A converters 65a to 65c, respectively (step S37).

When the above-described process ends, the value of the detection signal Y2 is compared with the value "0" (step S38). When the value of the detection signal Y2 is larger than the value "0" (Y2>0), a process of decreasing the initial value Q of the address is performed (step S39), and then, the initialization process is performed again (step S32). In contrast, when the value of the detection signal Y2 is smaller than the value "0" (Y2<0), a process of incrementing the initial value Q of the address is performed (step S40), and then, the initialization process is performed again (step S32). When the value of the detection signal Y2 is equal to the value "0" (Y2=0), the initialization process is performed again without changing the initial value Q of the address (step S32). The processes of steps S32 to S39 shown in FIG. 9 are performed repeatedly at a predetermined cycle (for example, 1 [msec]).

In this way, the CPU 64 performs a process of adjusting a readout address of the memory 63 according to the value of the detection signal Y2. When this process is performed, the phases of the data arrays L(i), M(i), N(i), and P(i) read from the memory 63 are changed. When such a process is performed repeatedly and the value of the detection signal Y2 reaches zero, the data arrays L(i), M(i), and P(i) read from the memory 63 to the CPU 64 become identical to the data arrays L(i), M(i), and P(i) read from the memory 52 to the CPU 53. In this way, the CPU 64 performs the lock-in detection using the reference signal (the data arrays L(i), M(i), and P(i)) of which the frequency and the phase are identical to those of the modulation signals MD1 to MD3 output from the CPU 53. In this way, variations of the detection signals X1 to X3 are prevented.

As described above, in the present embodiment, the same data arrays L(i), M(i), and P(i) as the data arrays L(i), M(i), and P(i) used for generating the modulation signals MD1 to MD3 in the upper head 20 are stored in the memory 63 of the lower head 30, and the data array N(i) of which the phase is different by 90° from that of the data array M(i) is stored in the memory 63 of the lower head 30. The readout address of the memory 63 is adjusted so as to change the phase of the reference signal so that the detection signal Y2 for which lock-in detection is performed using the data array N(i) reaches zero.

Due to this, even when a reference signal is not transferred from the upper head 20 to the lower head 30, it is possible to detect a plurality of signal components (the detection signals X1 to X3) included in the optical signal output from the optical receiver 31 with high accuracy. In the present embodiment, since the function of a dual-phase lock-in amplifier is realized by the CPU 64, it is possible to realize a small-size, lightweight, and low-cost device without increasing the size, the weight, and the cost.

In FIG. 7 showing the contents of the memories 52 and 53 in FIG. 6, in order to facilitate understanding, the phases of the data arrays L(i), M(i), N(i), and P(i) at i=0 are the same. When such a phase relation is employed, the peaks of the optical outputs emitted from the light emitters 25a to 25c may overlap each other and the peak of the amount of light received by the optical receiver 31 may increase. In order to prevent this, the phases of the data arrays L(i), M(i), N(i), and P(i) may be shifted appropriately. The data arrays M(i) and N(i) may maintain a phase difference relation of 90°.

While the signal detection device and the optical characteristics measurement device according to the embodiment of the present invention have been described, the present invention is not limited to the embodiment and may be freely modified within the scope of the present invention. For example, a combination of the upper head 20 and the lower head 30 in the first to third embodiments is not fixed and the combination may be changed freely. For example, the upper head 20 shown in FIG. 2 and the lower head 30 shown in FIG. 6 may be combined, or the lower head 30 shown in FIG. 2 and the upper head 20 shown in FIG. 6 may be combined.

Moreover, the moisture meter 1 as the optical characteristics measurement device described in the embodiment has the upper head 20 disposed on the upper surface of the paper P and the lower head 30 disposed on the rear surface of the paper P and receives light having passed through the paper P to measure the optical characteristics of the paper P. However, the upper head 20 and the lower head 30 may be disposed on either one of the upper surface or the rear surface of the paper P to receive light reflected or scattered by the paper P to measure the optical characteristics of the paper P. Furthermore, although an example of detecting three signal components included in the optical signal has been described in the embodiment, two or more signal components may be included in the optical signal.

What is claimed is:

1. A signal detection device comprising:
   a receiver configured to receive a signal including at least a first signal component modulated by a first frequency and a second signal component modulated by a second frequency; and
   a detector configured to:
      generate, using a base signal, a first reference signal to be used for detecting the first signal component and a second reference signal to be used for detecting the second signal component;
      perform lock-in detection on the signal received by the receiver using the first reference signal to obtain a first detection signal;
      perform lock-in detection on the signal received by the receiver using the second reference signal to obtain two second detection signals having different phases from each other; and
      change at least one of a frequency and a phase of each of the first and second reference signals to set one of the two second detection signals to zero.

2. The signal detection device according to claim 1, wherein
   the detector comprises:
   a reference oscillator configured to oscillate the base signal of which the frequency is variable;
   a divider configured to perform frequency dividing of the base signal to generate the first and second reference signals;
   a first lock-in amplifier configured to multiply the first reference signal output from the divider by the signal received by the receiver to generate the first detection signal; and
   a second lock-in amplifier configured to multiply the second reference signal output from the divider by the signal received by the receiver to generate the two second detection signals, and the reference oscillator is controlled to change the frequency of the base signal to change the at least one of the frequency and the phase of each of the first and second reference signals.

3. The signal detection device according to claim 2, wherein the second lock-in amplifier is configured to multiply the second reference signal output from the divider by the signal received by the receiver and multiply a third reference signal, which is obtained by shifting the phase of the second reference signal, by the signal received by the receiver to generate the two second detection signals having different phases from each other.

4. The signal detection device according to claim 3, wherein the second lock-in amplifier is configured to input the second detection signal generated by multiplying the third reference signal by the signal received by the receiver into the reference oscillator.

5. The signal detection device according to claim 4, wherein the reference oscillator is configured to change the frequency of the base signal to set the second detection signal input from the second lock-in amplifier to zero.

6. The signal detection device according to claim 1, wherein the first and second reference signals have different frequencies from each other.

7. The signal detection device according to claim 1, wherein the detector comprises:
a reference oscillator configured to oscillate the base signal of which the frequency is variable; and
a dual-phase lock-in amplifier configured to operate in synchronization with the base signal to generate the second detection signals,
the dual-phase lock-in amplifier comprises:
a digital converter configured to convert the signal received by the receiver to a digital signal;
a memory storing a sine wave data array and a cosine wave data array to be used as the second reference signal;
a first multiplier configured to sequentially read one of the sine wave data array and the cosine wave data array from the memory and multiply the read data array by the digital signal to generate one of the second detection signals;
a second multiplier configured to sequentially read the other of the sine wave data array and the cosine wave data array from the memory and multiply the read data array by the digital signal to generate the other of the second detection signals;
a first analog converter configured to convert the one of the second detection signals to an analog signal, and
a second analog converter configured to convert the other of the second detection signals to an analog signal, and
the reference oscillator is controlled to change the frequency of the base signal, and an operating frequency of the dual-phase lock-in amplifier is changed to change a readout speed of the sine wave data array and the cosine wave data array from the memory to thereby change the at least one of the frequency and the phase of the second reference signal.

8. The signal detection device according to claim 7, wherein the dual-phase lock-in amplifier further comprises:
a first adder configured to add multiplication results output from the first multiplier and average the addition result to generate the one of the second detection signals; and
a second adder configured to add multiplication results output from the second multiplier and average the addition result to generate the other of the second detection signals.

9. The signal detection device according to claim 8, wherein the second adder is configured to input the other of the second detection signals into the reference oscillator.

10. The signal detection device according to claim 9, wherein the reference oscillator is configured to change the frequency of the base signal to set the second detection signal input from the second adder to zero.

11. The signal detection device according to claim 1, wherein the detector comprises:
a digital converter configured to convert the signal received by the receiver to a digital signal;
a storage storing a first data array which includes a sine wave data array or a cosine wave data array to be used as the first reference signal and a second data array which includes a sine wave data array and a cosine wave data array to be used as the second reference signal; and
a processor configured to:
sequentially read the first data array and the second data array from the storage;
perform first multiplication of the first data array and the digital signal, second multiplication of the digital signal and the sine wave data array included in the second data array, and third multiplication of the digital signal and the cosine wave data array included in the second data array; and
adjust a readout address from the storage according to a multiplication result of the second or third multiplication to change the at least one of the frequency and the phase of each of the first reference signal and the second reference signal.

12. The signal detection device according to claim 1, wherein the receiver includes an optical receiver configured to receive at least first light of a first wavelength modulated by the first frequency and second light of a second wavelength modulated by the second frequency to output a signal including the first signal component and the second signal component.

13. An optical characteristics measurement device that measures optical characteristics of a measurement target, comprising:

an illumination device configured to irradiate first light of a first wavelength modulated by a first frequency and second light of a second wavelength modulated by a second frequency to the measurement target; and
a signal detection device, comprising:
an optical receiver configured to receive the first light of the first wavelength and the second light of the second wavelength having passed through the measurement target; and
a detector configured to:

generate, using a base signal, a first reference signal to be used for detecting the first light of the first wavelength and a second reference signal to be used for detecting the second light of the second wavelength;

perform lock-in detection on a signal of the light received by the optical receiver using the first reference signal to obtain a first detection signal;

perform lock-in detection on a signal of the light received by the optical receiver using the second reference signal to obtain two second detection signals having different phases from each other; and change at least one of a frequency and a phase of each of the first and second reference signals to set one of the two second detection signals to zero.

14. The optical characteristics measurement device according to claim 13, wherein
the detector comprises:
a reference oscillator configured to oscillate the base signal of which the frequency is variable;
a divider configured to perform frequency dividing of the base signal to generate the first and second reference signals;
a first lock-in amplifier configured to multiply the first reference signal output from the divider by the signal of the light received by the optical receiver to generate the first detection signal; and
a second lock-in amplifier configured to multiply the second reference signal output from the divider by the signal of the light received by the optical receiver to generate the two second detection signals, and
the reference oscillator is controlled to change the frequency of the base signal to change the at least one of the frequency and the phase of each of the first and second reference signals.

15. The optical characteristics measurement device according to claim 14, wherein
the second lock-in amplifier is configured to multiply the second reference signal output from the divider by the signal of the light received by the optical receiver and multiply a third reference signal, which is obtained by shifting the phase of the second reference signal, by the signal of the light received by the optical receiver to generate the two second detection signals having different phases from each other.

16. The optical characteristics measurement device according to claim 15, wherein
the second lock-in amplifier is configured to input the second detection signal generated by multiplying the third reference signal by the signal of the light received by the optical receiver into the reference oscillator.

17. The optical characteristics measurement device according to claim 16, wherein
the reference oscillator is configured to change the frequency of the base signal to set the second detection signal input from the second lock-in amplifier to zero.

18. The optical characteristics measurement device according to claim 13, wherein
the detector comprises:
a reference oscillator configured to oscillate the base signal of which the frequency is variable; and
a dual-phase lock-in amplifier configured to operate in synchronization with the base signal to generate the second detection signals,
the dual-phase lock-in amplifier comprises:

a digital converter configured to convert a signal of the light received by the optical receiver to a digital signal;
a memory storing a sine wave data array and a cosine wave data array to be used as the second reference signal;
a first multiplier configured to sequentially read one of the sine wave data array and the cosine wave data array from the memory and multiply the read data array by the digital signal to generate one of the second detection signals;
a second multiplier configured to sequentially read the other of the sine wave data array and the cosine wave data array from the memory and multiply the read data array by the digital signal to generate the other of the second detection signals;
a first analog converter configured to convert the one of the second detection signals to an analog signal; and
a second analog converter configured to convert the other of the second detection signals to an analog signal, and
the reference oscillator is controlled to change the frequency of the base signal, and an operating frequency of the dual-phase lock-in amplifier is changed to change a readout speed of the sine wave data array and the cosine wave data array from the memory to thereby change the at least one of the frequency and the phase of the second reference signal.

19. The optical characteristics measurement device according to claim 13, wherein
the detector comprises:
a digital converter configured to convert a signal of the light received by the optical receiver to a digital signal;
a storage storing a first data array which includes a sine wave data array or a cosine wave data array to be used as the first reference signal and a second data array which includes a sine wave data array and a cosine wave data array to be used as the second reference signal; and
a processor configured to:
sequentially read the first data array and the second data array from the storage;
perform first multiplication of the first data array and the digital signal, second multiplication of the digital signal and the sine wave data array included in the second data array, and third multiplication of the digital signal and the cosine wave data array included in the second data array; and
adjust a readout address from the storage according to a multiplication result of the second or third multiplication to change the at least one of the frequency and the phase of each of the first reference signal and the second reference signal.

20. An optical characteristics measurement device that measures optical characteristics of a measurement target, comprising:
an illumination device configured to irradiate first light of a first wavelength modulated by a first frequency and second light of a second wavelength modulated by a second frequency to the measurement target; and
a signal detection device, comprising:
an optical receiver configured to receive the first light of the first wavelength and the second light of the second wavelength reflected or scattered by the measurement target; and
a detector configured to:
generate, using a base signal, a first reference signal to be used for detecting the first light of the first wavelength and a second reference signal to be used for detecting the second light of the second wavelength;

perform lock-in detection on a signal of the light received by the optical receiver using the first reference signal to obtain a first detection signal;

perform lock-in detection on a signal of the light received by the optical receiver using the second reference signal to obtain two second detection signals having different phases from each other; and change at least one of a frequency and a phase of each of the first and second reference signals to set one of the two second detection signals to zero.

* * * * *